United States Patent [19]

Hasebe et al.

[11] Patent Number: 5,382,735
[45] Date of Patent: Jan. 17, 1995

[54] METHOD OF PREPARING ALKYLNAPHTHALENE COMPOUNDS

[75] Inventors: Ren Hasebe, Suita; Norimasa Okuda, Kyoto; Noboru Saito, Takatsuki, all of Japan

[73] Assignee: Nippon Shokubai Kagaku Kogyo Company, Limited, Osaka, Japan

[21] Appl. No.: 123,984

[22] Filed: Sep. 21, 1993

Related U.S. Application Data

[63] Continuation of Ser. No. 981,990, Nov. 24, 1992, abandoned, which is a continuation of Ser. No. 649,070, Feb. 1, 1991, abandoned.

[30] Foreign Application Priority Data

Feb. 2, 1990 [JP] Japan ................................ 2-22043
Jan. 29, 1991 [JP] Japan ................................ 3-009365

[51] Int. Cl.$^6$ ................................................ C07C 2/70
[52] U.S. Cl. ........................................ 585/467; 585/466
[58] Field of Search ............................ 585/446, 466, 467

[56] References Cited

U.S. PATENT DOCUMENTS 2,346,657 10/1967 Henke et al. ..................... 260/671
3,346,657 10/1967 Heuke et al. ..................... 585/446
4,689,436 8/1987 Minokani et al. .................. 585/422

FOREIGN PATENT DOCUMENTS 61-221136 10/1986 Japan .
62-255440 11/1987 Japan .
9003961 4/1990 WIPO .

OTHER PUBLICATIONS

"Catalysis by Heterogeneous Supported Heteropoly Acid" Yusuke Izumi, Ren Hasebe & Kazuo Urabe—Journal of Catalysis 84/1983 by Academic Press, Inc.
Chemical Abstracts, vol. 110, No. 9, p. 602 (1989), Abstract: 75023h; The American Chemical Society.

*Primary Examiner*—Asok Pal
*Assistant Examiner*—P. Achutamurthy
*Attorney, Agent, or Firm*—Birch, Stewart, Kolasch & Birch

[57] ABSTRACT

A method of preparing alkylnaphthalene compounds by reaction of a compound of naphthalene or monoalkylnaphthalene with olefin in the presence of a heteropoly acid catalyst. The method enables to produce highly valuable 2-monosubstituted alkylnaphthalene compounds or 2,6-disubstituted alkylnaphthalene compounds, in a high selectivity and a high yield. The used catalyst may be readily recovered and re-utilized.

6 Claims, No Drawings

METHOD OF PREPARING ALKYLNAPHTHALENE COMPOUNDS

This application is a continuation of application Ser. No. 07/981,990 filed on Nov. 24, 1992, now abandoned, which was a Rule 62 continuation application of Ser. No. 07/649,070, filed on Feb. 1, 1991, now abandoned.

FIELD OF THE INVENTION

The present invention relates to a method of preparing alkylnaphthalene compounds by reacting a naphthalene or a monoalkylnaphthalene with an olefin.

BACKGROUND OF THE INVENTION

Alkylnaphthalene compounds are important heating media and solvents for pressure sensitive paper, and thus are used extensively. Alkylnaphthalene compounds are also widely used in the manufacture of naphthalenedicarboxylic acid, and have recently received attention as raw materials for polyester, and naphthol compounds.

There are various alkylnaphthalene compounds (e.g., depending upon the position of the alkyl group substituent). However, 2-position-monosubstituted alkylnaphthalene compounds and 2,6-position-disubstituted alkylnaphthalene compounds are particularly useful.

Methods of preparing alkylnaphthalene compounds which have been generally adopted in the conventional art consist of reacting a compound of naphthalene or a monoalkylnaphthalene with an olefin in the presence of a catalyst composed of a Lewis acid such as $AlCl_3$, $BF_3$, etc., such as disclosed in Japanese Publication for Unexamined Patent Application No. 230645/1988, No. 61435/1989 and No. 197447/1989 (Tokukaisho No. 63-230645 and No. 64-61435, Tokukaihei No. 1-197447). However, these methods suffer from various drawbacks. For instance, the recovery and re-utilization of the catalyst employed is difficult and the strong corrosiveness of the catalyst restricts the materials use with industrial equipment. Also, among the different alkylnaphthalene compounds, 2-position-monosubstituted alkylnaphthalene compounds and 2,6-position-disubstituted alkylnaphthalene compounds are particularly valuable, as stated earlier. However, with the above described methods, isomerization is likely to take place during the chemical reaction, thereby giving rise to a large amount of 1-position-monosubstituted alkylnaphthalene compounds.

Some methods employ a silica-alumina catalyst or a zeolite catalyst instead of Lewis acid, such as disclosed kn Japanese Publication for Unexamined Patent Application No. 215647/1988, No. 9942/1989 and No. 135731/1989 (Tokukaisho No. 63-215647, No. 64-9942 and Tokukaihei No. 1-135731). However, these methods present industrial problems. For example, conversion, that denotes the proportion of raw material consumed, as well as the yield of the desired chemical compounds, are low whereby a large amount of catalyst is needed. In addition, isomerization is likely to take place.

SUMMARY OF THE INVENTION

An object of the present invention is to provide a method of preparing alkylnaphthalene compounds by reacting a compound of naphthalene or a monoalkylnaphthalene with an olefin. More specifically, the object of the present invention is to provide a method of preparing highly valuable 2-position-monosubstituted alkylnaphthalene compounds and 2,6-position-disubstituted alkylnaphthalene compounds, in a high selectivity and a high yield, and in such a manner that the catalyst used in the reaction may readily be recovered and re-utilized.

The inventors have found that, compared with the conventional catalysts cited above, the use of a heteropoly acid as catalyst enables a highly selective preparation having a remarkable high yield, and after intensive research brought the present invention to completion. Namely, the present invention consists in a method of preparing alkylnaphthalene compounds of the general formula [III]

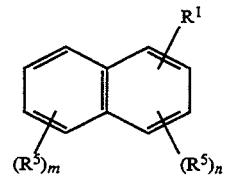

(wherein
$R^1$ represents a hydrogen atom or an alkyl group consisting of 1 to 4 carbons,
$R^2$, $R^3$, $R^4$ respectively represent either a hydrogen atom, a methyl group or an ethyl group,
$R^5$ represents a $—(R^2)(R^3)C—CH_2R^4$ group, and
m and n respectively represent 0 or a positive integer satisfying $1 \leq m+n \leq 4$ when $R^1$ represents a hydrogen atom, and 0 or a positive integer satisfying $1 \leq m+n \leq 3$ when $R^1$ represents an alkyl group consisting of 1 to 4 carbons) by reacting a compound of a naphthalene or a monoalkylnaphthalene of the general formula [I]

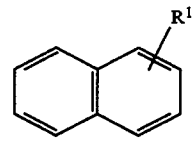

with an olefin of the general formula [II]

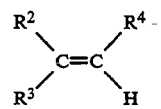

in the presence of a catalyst composed of a heteropoly acid.

The compound of naphthalene or monoalkylnaphthalene of the formula [I] may be: naphthalene, 1-methylnaphthalene, 2-methylnaphthalene, 1-ethylnaphthalene, 2-ethylnaphthalene, 1-isopropylnaphthalene, 2-isopropylnaphthalene, 2-sec-butylnaphthalene, 2-tert-butylnaphthalene, or other compounds. As to the olefin of the formula [II], ethylene, propylene, 1-butene, cis-2-butene, trans-2-butene, isobutylene, etc., may be employed.

Among the various heteropoly acids that can be adopted as catalyst, heteropoly acids of the general formula $H_aX_1Y_{12}O_{40}$ (wherein X represents phosphorus or silicon, Y represents at least one kind of element selected from the group consisting of tungsten, molybdenum and vanadium, and a represents a numerical value determined according to X and Y) are preferred for their excellent catalytic performance. The above heteropoly acids may be, for example: 12-tungstophosphoric acid ($H_3PW_{12}O_{40}$), 12-tungstosilicic acid ($H_4SiW_{12}O_{40}$), 12-molybdophosphoric acid ($H_3PMo_{12}O_{40}$), 12-molybdosilicic acid ($H_4SiMo_{12}O_{40}$), a tungstomolybdophosphoric acid ($H_3PW_{12-x}Mo_xO_{40}$, wherein x is in the range of $0 < X < 12$) consisting of a co-ordinated mixture of tungsten and molybdenum, a molybdovanadophosphoric acid ($H_{3+x}PMo_{12}V_xO_{40}$, wherein x is in the range of $0 < X < 12$) consisting of a co-ordinated mixture of molybdenum and vanadium, etc.

Commercially available heteropoly acid may be used for the reaction without any treatment. However, the heteropoly acid should preferably be supported by impregnation on a support to facilitate its separation and recovery after the reaction is completed. The support should preferably be selected from the group consisting of silica, titania, active carbon, etc. that are stable with respect to heteropoly acid and have a large surface area. The catalyst should preferably be calcined at a temperature above the temperature of the reaction of the compound of naphthalene or monoalkylnaphthalene and olefin. The temperature of the calcination varies according to the kind of heteropoly acid, but should be in the range of 100° to 600° C., preferably 150° to 500° C.

The reaction may be conducted under liquid phase or vapor phase conditions.

The case of a liquid phase reaction will be discussed first. In a reaction vessel are placed the compound of naphthalene or monoalkylnaphthalene of the formula [I] and olefin of the formula [II], and a predetermined amount of heteropoly acid is added. The mixture is heated with stirring to a predetermined temperature to cause the reaction. The amount of catalyst employed should be approximately 1 to 10% by weight based on the compound of naphthalene or monoalkylnaphthalene used as raw material. The temperature of the reaction should preferably be in the range of 100° to 300° C. In order to enable a smooth reaction, the compound of naphthalene or monoalkylnaphthalene serving as raw material may be dissolved or suspended in a solvent and diluted. A solvent that does not unfavorably affect the reaction is selected. For instance, saturated hydrocarbons such as, e.g., n-decane, n-undecane, n-dodecane, etc., may be employed. The molar ratio of the compound of naphthalene or monoalkylnaphthalene and olefin placed in the reaction vessel, is suitably determined according to the kinds of raw materials and catalyst employed, and according to the kinds of alkylnaphthalene compounds to be produced. When the alkylnaphthalene compounds to be produced are monoalkylated products obtained by addition of 1 mole of olefin to 1 mole of the compound of naphthalene or monoalkylnaphthalene, the molar ratio of the compound of naphthalene or monoalkylnaphthalene and olefin placed in the reaction vessel should be in the range of 1:0.1 to 1:2, preferably in the range of 1:0.5 to 1:1.2. When the alkylnaphthalene compounds to be produced are dialkylated products obtained by addition of 2 moles of olefin to 1 mole of the compound of naphthalene or monoalkylnaphthalene, the molar ratio should be in the range of 1:1 to 1:10, preferably in the range of 1:1.2 to 1:3. The above molar ratios enable to obtain the desired products with a high selectivity.

In the case of a vapor phase reaction, an ordinary fixed bed flow system reactor can be conveniently adopted. A reaction tube wherein a catalyst composed of heteropoly acid loaded on a support was filled, is heated to a predetermined reaction temperature. A mixed gas composed of the raw materials, i.e., the compound of naphthalene or monoalkylnaphthalene and olefin is poured into the reaction tube. An inert gas, such as nitrogen or other gas, is preferably employed as carrier gas since inert gas enables to regulate the reaction easily. The concentration of the compound of naphthalene or monoalkylnaphthalene contained in the mixed gas fed into the reaction tube should be in the range of 0.01 to 10% by volume, preferably in the range of 0.2 to 5% by volume. The molar ratio of olefin and the compound of naphthalene or monoalkylnaphthalene contained in the mixed gas is suitably determined as was discussed in the case of the liquid phase reaction. The reaction temperature should be in the range of 200° to 600° C., preferably in the range of 300° to 450° C. The space velocity should preferably be in the range of 1000 to 5000 $hr^{-1}$. The reaction pressure can be either normal pressure, elevated pressure or reduced pressure.

Compared with a conventional method, the method of preparing alkylnaphthalene compounds of the general formula [III] by reacting a compound of naphthalene or monoalkylnaphthalene of the general formula [I] with olefin of the general formula [II] in accordance with the present invention, enables to produce alkylnaphthalene compounds, in particular highly valuable 2-position-monosubstituted alkylnaphthalene compounds and 2,6-position-disubstituted alkylnaphthalene compounds in a high selectivity and a high yield. Especially, when 2-position-monosubstituted alkylnaphthalene is used as raw material, instances of isomerization giving rise to 1-substituted compounds are few. Meanwhile, when 1-monosubstituted alkylnaphthalene is adopted as raw material, a significant isomerization occurs to give rise to 2-substituted compounds. The method of the present invention thus enables to obtain the desired 2-substituted compounds in a large quantity. In addition, the catalyst may be recovered easily and re-utilized, and the problem of the corrosiveness of the catalyst is eliminated. The method of the present invention therefore offers industrial advantages.

The product obtained after the reaction is completed, may be suitably refined to extract the desired monoaddition products, diaddition products, etc.

Furthermore, when necessary, the residue obtained after the removal of the above desired products may be mixed to the raw materials of the reaction and re-utilized. This is particularly effective when, for example, the residue is chiefly composed of unreacted raw materials, or, in the case that diaddition products are the desired products, when the residue is chiefly composed of unreacted raw materials or of monoaddition products. Further, in the case that, for example, the residue is composed of polyaddition products in which the number of alkyl groups added is higher than that of the desired products, when the residue is mixed to the compound of naphthalene or monoalkylnaphthalene of the formula [I] and reaction is carried out again, the alkyl group of the naphthalene ring of the polyaddition product is shifted on the naphthalene ring of the compound of naphthalene or monoalkylnaphthalene of the formula [I]. This enables a large number of monoaddition and diaddition products to be obtained thereby improving the yield.

For a fuller understanding of the nature and advantages of the invention, reference should be made to the ensuing detailed description.

DETAILED DESCRIPTION OF THE INVENTION

The following embodiments will discuss the present invention in detail.

The conversion and selectivity mentioned in the embodiments conform to the following definitions.

conversion (mole percent) =

$$\frac{\text{number of moles of compound of naphthalene or monoalkylnaphthalene raw material consumed}}{\text{number of moles of compound of naphthalene or monoalkylnaphthalene raw material supplied}} \times 100$$

selectivity (mole percent) =

$$\frac{\text{number of moles of alkylnaphthalene obtained}}{\text{number of moles of compound of naphthalene or monoalkylnaphthalene raw material consumed}} \times 100$$

EXAMPLE 1

In a 100 ml autoclave were placed 10 g of naphthalene, 20 ml of n-undecane serving as solvent, 0.5 g of supported heteropoly acid serving as catalyst and obtained by loading 30% by weight of 12-tungstophosphoric acid on silica (ID gel manufactured by Fuji Davison), and 7 g of propylene. Hereinafter, the above defined heteropoly acid catalyst will be referred to as 30% by weight $PW_{12}/SiO_2$; the same expression will be used for other supported heteropoly acid catalysts. The mixture was heated with stirring and the reaction was performed at 200° C. for two hours. The reaction mixture was cooled and the heteropoly acid catalyst was separated therefrom by filtration to give a filtrate. No heteropoly acid was found to be dissolved in the filtrate. The liquid product was analyzed by gas chromatography and the conversion of naphthalene was found to be equal to 80 mole percent. Among the monoaddition products obtained, the selectivity of 2-isopropylnaphthalene (2-monosubstituted compound; hereinafter referred to as 2-IPN), was 20.5 mole percent, and the selectivity of 1-isopropylnaphthalene (1-monosubstituted compounds; hereinafter referred to as 1-IPN), was 0.5 mole percent. The selectivity of the diaddition product di-isopropylnaphthalene (hereinafter referred to as DIPN) was 72 mole percent. 55% of the DIPN consisted of 2,6-di-isopropylnaphthalene (2,6-disubstituted compound; hereinafter referred to as 2,6-DIPN).

The reaction conditions and results are respectively illustrated in Table 1 and Table 2.

EXAMPLE 2

The example 1 was repeated except using the heteropoly acid catalyst separated by filtration in example 1.

The reaction conditions and results are respectively illustrated in Table 1 and Table 2.

EXAMPLES 3 TO 7

The example 1 was repeated except using different catalysts.

The reactions conditions and results are respectively illustrated in Table 1 and Table 2.

EXAMPLE 8

The example 3 was repeated except that the amount of propylene is equal to 3 g and that the reaction was performed at 180° C. for one hour.

The reaction conditions and results are respectively illustrated in Table 1 and Table 2.

EXAMPLE 9

The example 1 was repeated except using 2-isopropylnaphthalene (having a purity equal to 98%) obtained in example 8 as raw material instead of naphthalene, and 20% by weight $PW_{12}/SiO_2$ as catalyst and that the reaction was performed at 240° C. The liquid product was analyzed by gas chromatography and the conversion of 2-IPN was found to be equal to 70 mole percent. The selectivity of the monoaddition product DIPN (disubstituted compound) was 93 mole percent. 72% of the DIPN consisted of 2,6-DIPN. The selectivity of 1-IPN produced by isomerization of 2-IPN was 0.2 mole percent.

The reaction conditions and results are respectively illustrated in Table 1 and Table 2.

EXAMPLE 10

The example 1 was repeated except that 2-methylnaphthalene (hereinafter referred to as 2-MN) was used as raw material instead of naphthalene, no solvent was employed, and 30 g of 2-MN and 10 g of propylene were placed. The liquid product was analyzed by gas chromatography and the conversion of 2-MN was found to be equal to 82 mole percent. The selectivity of the monoaddition product methyl isopropylnaphthalene (disubstituted compound; hereinafter referred to as MIPN) was 89 mole percent. 64% of the MIPN consisted of 2-methyl-6-isopropylnaphthalene (2,6-disubstituted compound; hereinafter referred to as 2,6-MIPN). The selectivity of 1-methylnaphthalene (hereinafter referred to as 1-MN) produced by isomerization of 2-MN was 0.5 mole percent.

The reaction conditions and results are respectively illustrated in Table 1 and Table 2.

Comparative Example 1

A silica-alumina catalyst was prepared as described below, following the instructions given in example 1 of Japanese Publication for Unexamined Patent Application No. 135731/1989 (Tokukaihei 1-135731).

To 3.2 g of aluminum sec-butoxide and 67.1 g of tetraethoxysilane in a 300 ml beaker there were added 0.79 g of dimethyl sulfate and 50.0 g of ethylene glycol. The mixture was stirred at 60° to 70° C. for three hours. 23.2 g of water was added to the resulting solution that was then stirred at 70° to 80° C. to produce a gelatinous gel. After crushing, the gel was dried at 110° C. under reduced pressure, finely ground and calcined at 550° C. for eight hours to produce the silica-alumina catalyst.

The reaction of 2-MN and propylene was performed in the same reaction conditions as the example 10 except using the above silica-alumina catalyst.

The reaction conditions and results are respectively illustrated in Table 1 and Table 2.

EXAMPLE 11

The example 1 was repeated except using 30 g of 2-MN instead of naphthalene and 3 g of ethylene instead of propylene as raw materials, and using n-decane instead of n-undecane as solvent. The reaction was performed at 220° C. for three hours. The liquid product was analyzed by gas chromatography and the conversion of 2-MN was found to De equal to 74 mole percent. The selectivity of the monoaddition product methylethylnaphthalene (disubstituted compound; hereinafter referred to as MEN) was 91 mole percent. 53% of MEN consisted of 2-methyl-6-ethylnaphthalene (2,6-disubstituted compound; hereinafter referred to as 2,6-MEN). The selectivity of 1-MN produced by isomerization of 2-MN was 2 mole percent.

The reaction conditions and results are respectively illustrated in Table 1 and Table 2.

EXAMPLE 12

The example 3 was repeated except using cis-2-butene instead of propylene as raw material, and n-decane instead of n-undecane as solvent. The liquid product was analyzed by gas chromatography and the conversion of naphthalene was found to be equal to 72 mole percent. Among the monoaddition products, the selectivity of 2-sec-butylnaphthalene (2-monosubstituted compound; hereinafter referred to as 2-SBN) was 20 mole percent, the selectivity of 1-sec-butylnaphthalene (1-monosubstituted compound; hereinafter referred to as 1-SBN) was 1 mole percent. The selectivity of the diaddition product di-sec-butylnaphthalene (hereinafter referred to as DSBN) was 64 mole percent. 59% of DSBN consisted of 2,6-di-sec-butylnaphthalene (2,6-disubstituted compound; hereinafter referred to as 2,6-DSBN).

The reaction conditions and results are respectively illustrated in Table 1 and Table 2.

EXAMPLE 13

The example 12 was repeated except using isobutylene instead of cis-2-butene as raw material. The liquid product was analyzed by gas chromatography and the conversion of naphthalene was found to be equal to 75 mole percent. Among the monoaddition products, the selectivity of 2-tert-butylnaphthalene (2-monosubstituted compound; hereinafter referred to as 2-TBN) was 22 mole percent, and the selectivity of 1-tert-butylnaphthalene (1-monosubstituted compound; hereinafter referred to as 1-TBN) was 0.8%. The selectivity of the diaddition product di-tert-butylnaphthalene (hereinafter referred to as DTBN) was 65 mole percent. 60% of DTBN consisted of 2,6-di-tert-butylnaphthalene (2,6-disubstituted compound; hereinafter referred to as 2,6-DTBN).

The reaction conditions and results are respectively illustrated in Table 1 and Table 2.

EXAMPLE 14

The example 3 was repeated except placing 14 g of propylene and performing the reaction for three hours.

The reaction conditions and results are respectively illustrated in Table 1 and Table 2.

TABLE 1

| | | | Reaction conditions | | | | |
|---|---|---|---|---|---|---|---|
| | Catalyst placed amount | Compound [I]* placed amount | Olefin [II] placed amount | Molar ratio [II]/[I] | Solvent placed amount | Reac. temp. °C. | Reac. time hr |
| Ex 1 | 30 wt % $PW_{12}/SiO_2$ 0.5 g | naphthalene 10 g | propylene 7 g | 2.13 | n-undecane 20 ml | 200 | 2 |
| Ex 2 | 30 wt % $PW_{12}/SiO_2$ filtered from Ex. 1 | naphthalene 10 g | propylene 7 g | 2.13 | n-undecane 20 ml | " | " |
| Ex 3 | 30 wt % $SiW_{12}/SiO_2$ 0.5 g | naphthalene 10 g | propylene 7 g | 2.13 | n-undecane 20 ml | " | " |
| Ex 4 | 30 wt % $PMo_{12}/SiO_2$ 0.5 g | naphthalene 10 g | propylene 7 g | 2.13 | n-undecane 20 ml | " | " |
| Ex 5 | 30 wt % $SiMo_{12}/SiO_2$ 0.5 g | naphthalene 10 g | propylene 7 g | 2.13 | n-undecane 20 ml | " | " |
| Ex 6 | 30 wt % $PMo_6W_6/SiO_2$ 0.5 g | naphthalene 10 g | propylene 7 g | 2.13 | n-undecane 20 ml | " | " |
| Ex 7 | 30 wt % $PMo_{11}V/SiO_2$ 0.5 g | naphthalene 10 g | propylene 7 g | 2.13 | n-undecane 20 ml | " | " |
| Ex 8 | 30 wt % $SiW_{12}/SiO_2$ 0.5 g | naphthalene 10 g | propylene 3 g | 0.91 | n-undecane 20 ml | 180 | 1 |
| Ex 9 | 20 wt % $PW_{12}/SiO_2$ 0.5 g | 2-IPN 10 g | propylene 3 g | 1.21 | n-undecane 20 ml | 240 | 2 |
| Ex 10 | 30 wt % $PW_{12}/SiO_2$ 0.5 g | 2-MN 30 g | propylene 10 g | 1.13 | none | 200 | 2 |
| Cp Ex 1 | silica-alumina 0.5 g | 2-MN 30 g | propylene 10 g | " | " | " | " |
| Ex 11 | 30 wt % $PW_{12}/SiO_2$ 0.5 g | 2-MN 30 g | ethylene 3 g | 0.51 | n-decane 25 ml | 220 | 3 |
| Ex 12 | 30 wt % $SiW_{12}/SiO_2$ 0.5 g | naphthalene 10 g | cis-2-butene 7 g | 1.60 | n-decane 20 ml | 180 | 1 |

TABLE 1-continued

| | Catalyst placed amount | Compound [I]* placed amount | Olefin [II] placed amount | Molar ratio [II]/[I] | Solvent placed amount | Reac. temp. °C. | Reac. time hr |
|---|---|---|---|---|---|---|---|
| Ex 13 | 30 wt % SiW$_{12}$/SiO$_2$ 0.5 g | naphthalene 10 g | isobutylene 7 g | " | n-decane 20 ml | " | " |
| Ex 14 | 30 wt % SiW$_{12}$/SiO$_2$ 0.5 g | naphthalene 10 g | propylene 14 g | 4.26 | n-undecane 20 ml | 200 | 3 |

*Compound of naphthalene or monoalkylnaphthalene

TABLE 2

| | [I] Conversion mol % | [I] Selectivity (mol %) 2-monosubs. comp. | [I] Selectivity (mol %) 1-monosubs. comp. | [I] Selectivity (mol %) disubs. comp. | 2,6-disubs. comp. among disubs. comp. (%) |
|---|---|---|---|---|---|
| Ex 1 | 80 | 2-IPN 20.5 | 1-IPN 0.5 | DIPN 72 | 2,6-DIPN 55 |
| Ex 2 | 81 | 2-IPN 21 | 1-IPN 0.4 | DIPN 73 | 2,6-DIPN 54 |
| Ex 3 | 85 | 2-IPN 16 | 1-IPN 1 | DIPN 74 | 2,6-DIPN 53 |
| Ex 4 | 62 | 2-IPN 35 | 1-IPN 3 | DIPN 59 | 2,6-DIPN 46 |
| Ex 5 | 56 | 2-IPN 45 | 1-IPN 3 | DIPN 50 | 2,6-DIPN 45 |
| Ex 6 | 73 | 2-IPN 27.5 | 1-IPN 1.5 | DIPN 66 | 2,6-DIPN 49 |
| Ex 7 | 64 | 2-IPN 35.5 | 1-IPN 1.5 | DIPN 60 | 2,6-DIPN 50 |
| Ex 8 | 79 | 2-IPN 90 | 1-IPN 2 | DIPN 8 | 2,6-DIPN 57 |
| Ex 9 | 70 | — | 1-IPN 0.2 | DIPN 93 | 2,6-DIPN 72 |
| Ex 10 | 82 | — | 1-MN 0.5 | MIPN 89 | 2,6-MIPN 64 |
| Cp Ex 1 | 23 | — | 1-MN 13 | MIPN 80 | 2,6-MIPN 38 |
| Ex 11 | 74 | — | 1-MN 2 | MEN 91 | 2,6-MEN 53 |
| Ex 12 | 72 | 2-SBN 20 | 1-SBN 1 | DSBN 64 | 2,6-DSBN 59 |
| Ex 13 | 75 | 2-TBN 22 | 1-TBN 0.8 | DTBN 65 | 2,6-DTBN 60 |
| Ex 14 | 88 | 2-IPN 2.5 | 1-IPN 0.1 | DIPN 26 | 2,6-DIPN 52 |
| | | trisubs. comp. 63% | | tetrasubs. comp. 6% | |

EXAMPLE 15

20 cc of a catalyst (9 to 20 mesh) having the same composition as that of example 1 was filled in a reaction tube having a bore diameter equal to 10 mm and heated to 300° C. A raw material gas composed of 2% by volume of naphthalene, 6% by volume of propylene and 92% by volume of nitrogen, was flown at a space velocity of 1500 hr$^{-1}$ and the reaction was performed at a temperature of 300° C.

The reaction conditions are shown in Table 3, and the results of the analysis of the gas given one hour after the start of the reaction are shown in Table 4.

EXAMPLE 16

The example 15 was repeated using 30% by weight SiW$_{12}$/SiO$_2$ instead of 30% by weight PW$_{12}$/SiO$_2$ as catalyst. A raw material gas composed of 2% by volume of 2-MN, 2.5% by volume of propylene and 95.5% by volume of nitrogen was flown at a space velocity of 2000 hr$^{-1}$ and the reaction was performed at a temperature of 320° C.

The reaction conditions and results are respectively illustrated in Table 3 and Table 4.

EXAMPLE 17

The example 16 was repeated except using 1-MN instead of 2-MN. The reaction product obtained was analyzed by gas chromatography and the conversion of 1-MN was found to be 73 mole percent. There was observed a significant amount of 2-MN produced due to the isomerization of the 1-MN raw material. The selectivity of 2-MN obtained was 11 mole percent. The selectivity of the monoaddition product MIPN (disubstituted compound) was 79 mole percent, and 39% of MIPN consisted of 2,6-MIPN.

The reaction conditions and results are respectively illustrated in Table 3 and Table 4.

EXAMPLE 18

The example 15 was repeated using 20% by weight PW$_{12}$/SiO$_2$ instead of 30% by weight PW$_{12}$/SiO$_2$ as catalyst. A raw material gas composed of 1% by volume of naphthalene, 10% by volume of ethylene and 89% by volume of nitrogen, was flown at a space velocity of 1200 hr$^{-1}$ and the reaction was performed at a temperature of 350° C. The reaction product obtained was analyzed by gas chromatography and the conversion of naphthalene was found to be equal to 59 mole percent. Among the monoaddition products, the selectivity of 2-ethylnaphthalene (2-monosubstituted compound; hereinafter referred to as 2-EN) was 42 mole percent, and the selectivity of 1-ethylnaphthalene (1-monosubstituted compound; hereinafter referred to as 1-EN) was 4 mole percent. The selectivity of the diaddition product diethylnaphthalene (hereinafter referred to as DEN) was 49 mole percent. 43% of DEN consisted of 2,6-diethylnaphthalene (2,6-disubstituted compound; hereinafter referred to as 2,6-DEN).

The reaction conditions and results are respectively illustrated in Table 3 and Table 4.

The invention being thus described, it will be obvious that the same may be varied in many ways. Such variations are not to be regarded as a departure from the scope of the invention.

There are described above novel features which the skilled man will appreciate give rise to advantages. These are each independent aspects of the invention to be covered by the present application, irrespective of whether or not they are included within the scope of the following claims.

TABLE 3

| | Catalyst placed amount | Compound [I]* vol % | Olefin [II] vol % | Molar ratio [II]/[I] | Reaction temp. °C. | Space velocity hr$^{-1}$ |
|---|---|---|---|---|---|---|
| | | | Reaction conditions | | | |
| Ex 15 | 30 wt % PW$_{12}$/SiO$_2$ 20 cc | naphthalene 2 | propylene 6 | 3 | 300 | 1500 |
| Ex 16 | 30 wt % SiW$_{12}$/SiO$_2$ 20 cc | 2-MN 2 | propylene 2.5 | 1.25 | 320 | 2000 |
| Ex 17 | 30 wt % SiW$_{12}$/SiO$_2$ 20 cc | 1-MN 2 | propylene 2.5 | " | " | " |
| Ex 18 | 20 wt % PW$_{12}$/SiO$_2$ 20 cc | naphthalene 1 | ethylene 10 | 10 | 350 | 1200 |

*Compound of naphthalene or monoalkylnaphthalene

TABLE 4

| | [I] Conversion mol % | 2-mono-subs. comp. | 1-mono-subs. comp. | disubs. comp. | 2,6-disubs. comp. among disubs. comp. (%) |
|---|---|---|---|---|---|
| | | Reaction results | | | |
| | | [I] Selectivity (mol %) | | | |
| Ex 15 | 78 | 2-IPN 18 | 1-IPN 1 | DIPN 72 | 2,6-DIPN 52 |
| Ex 16 | 80 | — | 1-MN 0.6 | MIPN 87 | 2,6-MIPN 61 |
| Ex 17 | 73 | 2-MN 11 | — | MIPN 79 | 2,6-MIPN 39 |
| Ex 18 | 59 | 2-EN 42 | 1-EN 4 | DEN 49 | 2,6-DEN 43 |

What is claimed is:

1. A method of preparing a 2,6-dialkylnaphthalene compound of the general formula

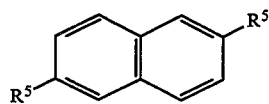

by reacting in a reaction zone a naphthalene compound of the general formula

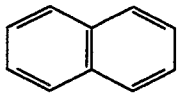

with an olefin of the general formula

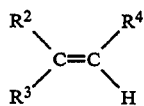

in the presence of a catalyst composed of a heteropoly acid, wherein

R$^5$ is —(R$^2$)(R$^3$)C—CH$_2$R$^4$;

R$^2$, R$^3$, R$^4$ respectively are either a hydrogen atom, a methyl group or an ethyl group; and wherein the molar ratio of the naphthalene compound to the olefin is in the range of 1:1.6 to 1:10, and the reaction is performed at a temperature in the range of 180° C. to 300° C. while maintaining a liquid phase in the reaction zone.

2. A method as defined in claim 1 wherein the general formula of the heteropoly acid is H$_a$X$_1$Y$_{12}$O$_{40}$, wherein X is phosphorus or silicon, Y is at least one element selected from the group consisting of tungsten, molybdenum and vanadium, and a is a numerical value which is consistent with the valency of X and Y so as to give a neutrally charged catalyst moiety.

3. A method as defined in claim 1 wherein the amount of the catalyst is 1 to 10% by weight based on the amount of the compound of naphthalene.

4. A method as defined in claim 1 wherein the reaction is performed at a temperature in the range of 200° C. to 600° C. while maintaining a vapor phase in the reaction zone.

5. A method as defined in claim 2 wherein the heteropoly acid is supported by impregnation on a support.

6. A method as defined in claim 5 wherein the support is silica, titania, or active carbon.